US008652512B2

(12) United States Patent
Schmehl et al.

(10) Patent No.: US 8,652,512 B2
(45) Date of Patent: Feb. 18, 2014

(54) NEBULIZED LIPOSOMES FOR THE PULMONARY APPLICATION OF DRUG COMPOUNDS

(75) Inventors: Thomas Schmehl, Giessen (DE); Tobias Gessler, Wettenberg (DE); Esther Waschkowitz, Giessen (DE)

(73) Assignee: United Therapeutics Corporation, Silver Spring, MD (US)

( * ) Notice: Subject to any disclaimer, the term of this patent is extended or adjusted under 35 U.S.C. 154(b) by 1814 days.

(21) Appl. No.: 10/510,040

(22) PCT Filed: Apr. 4, 2003

(86) PCT No.: PCT/DE03/01068
§ 371 (c)(1),
(2), (4) Date: Jun. 21, 2005

(87) PCT Pub. No.: WO03/084507
PCT Pub. Date: Oct. 16, 2003

(65) Prior Publication Data
US 2006/0002992 A1    Jan. 5, 2006

(30) Foreign Application Priority Data
Apr. 4, 2002   (DE) .................................. 102 14 983

(51) Int. Cl.
*A61K 9/127*   (2006.01)
(52) U.S. Cl.
USPC ....................................................... 424/450
(58) Field of Classification Search
USPC ....................................................... 424/450
See application file for complete search history.

(56) References Cited

U.S. PATENT DOCUMENTS

| | | | | |
|---|---|---|---|---|
| 4,732,914 A | * | 3/1988 | Morton, Jr. .................. | 514/530 |
| 4,895,719 A | | 1/1990 | Radhakrishnan et al. | |
| 5,006,343 A | | 4/1991 | Benson et al. | |
| 5,049,388 A | * | 9/1991 | Knight et al. ................. | 424/450 |
| 5,306,483 A | * | 4/1994 | Mautone ........................ | 424/45 |
| 5,340,587 A | * | 8/1994 | Mihalko et al. ............... | 424/450 |
| 5,580,575 A | | 12/1996 | Unger et al. | |
| 5,585,112 A | | 12/1996 | Unger et al. | |
| 5,662,929 A | | 9/1997 | Lagace et al. | |
| 5,715,824 A | | 2/1998 | Unger et al. | |
| 5,783,566 A | | 7/1998 | Mislick | |
| 5,814,335 A | * | 9/1998 | Webb et al. ................... | 424/450 |
| 6,113,946 A | | 9/2000 | Szoka, Jr. et al. | |
| 6,193,997 B1 | * | 2/2001 | Modi ............................. | 424/450 |
| 6,443,898 B1 | | 9/2002 | Unger et al. | |
| 6,764,693 B1 | | 7/2004 | Smith | |
| 6,793,912 B2 | | 9/2004 | Pilkiewicz et al. | |
| 7,138,136 B2 | | 11/2006 | Annapragada et al. | |
| 7,384,978 B2 | | 6/2008 | Phares et al. | |
| 7,417,070 B2 | | 8/2008 | Phares et al. | |
| 7,544,713 B2 | | 6/2009 | Phares et al. | |
| 2001/0055610 A1 | * | 12/2001 | Nagata et al. .................. | 424/450 |
| 2003/0059375 A1 | | 3/2003 | Perez-Soler et al. | |
| 2003/0232019 A1 | | 12/2003 | Basu et al. | |
| 2004/0009231 A1 | | 1/2004 | Jackson et al. | |
| 2005/0008617 A1 | | 1/2005 | Chen et al. | |
| 2005/0282901 A1 | | 12/2005 | Phares et al. | |
| 2006/0141029 A1 | | 6/2006 | Heller et al. | |
| 2006/0141047 A1 | | 6/2006 | Heller et al. | |
| 2007/0077290 A1 | | 4/2007 | Li et al. | |

FOREIGN PATENT DOCUMENTS

| | | |
|---|---|---|
| EP | 0 126 580 B1 | 11/1984 |
| EP | 0 361 894 | 9/1989 |
| WO | WO 86/06959 A1 | 12/1986 |
| WO | WO 8705803 A1 * | 10/1987 |
| WO | 02/03959 A1 | 1/2002 |
| WO | WO 2004/112695 A2 | 12/2004 |
| WO | WO 2006/012446 A2 | 11/2006 |
| WO | WO 2009/070609 A2 | 6/2009 |
| WO | WO 2009/127060 A1 | 10/2009 |
| WO | WO 2009/129395 A1 | 10/2009 |

OTHER PUBLICATIONS

JF Hunt, K Fang, R Malik, A Snyder, N Malhotra, TAE Platts-Mills, B Gaston. "Endogenous Airway Acidification: Implications for Asthma Pathophysiology." Am J Respir Crit Care Med. 2000; 161: pp. 694-699.*
KMG Taylor, JM Newton. "Liposomes for Controlled Delivery of Drugs to the Lung." Thorax, vol. 47, 1992, pp. 257-259.*
M Max, R Rossaint. "Inhalted Prostacyclin in the Treatment of Pulmonary Hypertension." European Journal of Pediatrics, vol. 158, Supplement 1, 1999, pp. S23-S26.*
Kleemann et al., "Iloprost-Containing Liposomes for Aerosol Application in Pulmonary Arterial Hypertension: Formulation Aspects and Stability," Pharmaceutical Research, Feb. 2007 (published online Dec. 27, 2006), 24(2):277-287.
U.S. Appl. No. 13/386,006, filed Jun. 29, 2010, Pollock et al.
M. Singh, et al., "Stealth monensin liposomes as a potentiator of adriamycin in cancer treatment", Journal of Controlled Release, Elsevier Science Publishers, vol. 59, No. 1, May 1, 1999.

* cited by examiner

*Primary Examiner* — Brian Gulledge
*Assistant Examiner* — Celeste A Roney
(74) *Attorney, Agent, or Firm* — Foley & Lardner LLP

(57) ABSTRACT

The present invention discloses a method to prepare specific liposomal formulations for the pulmonary application of therapeutic substances. The liposomal components, DPPC and cholesterol at a molar ratio of 7:3 and 7:4, respectively, are combined with the non-toxic excipients, sphingomyelin, dimyristoylphophatidylcholine and/or polyethylene glycol, to prepare liposomes that are stabile during nebulization with commercially available nebulizers and exhibit sustained release kinetics of encapsulated drug substances.

31 Claims, 4 Drawing Sheets

NEBULIZED LIPOSOMES FOR THE PULMONARY APPLICATION OF DRUG COMPOUNDS

FIELD OF THE INVENTION

There is disclosed a method for preparing liposomes that are stable during nebulization and are suitable for pulmonary application. The said liposomes release encapsulated drug compounds in a controlled manner.

BACKGROUND OF THE INVENTION

Within the field of pharmaceutical sciences, specialized dosage forms providing an extended duration of drug action are classified into several groups. While such formulations all share the common objective of prolonging the length of drug activity in the body, they may achieve this in various ways. The various subgroups include extended-, sustained-, delayed- and pulsed-release formulations. A controlled release profile can be obtained by chemical modification of the drug compound (i.e. salts, esters, complexes), by the use off pharmaceutical excipients, by varying formulation parameters (i.e. particle size, tablet hardness), as well as by the individual selection of the route and means of application.

The application of therapeutic drug compounds to the lung is especially challenging, as the organ's high sensitivity restricts the number of excipients suitable for pulmonary delivery and, further, a controlled, reproducible release in the lung is difficult to achieve. Liposomes are considered to be formulations with a high tolerance and little to no toxicity. This claim is based upon the excellent biocompatibility track-record established by several approved liposomal formulations already on the market, including the products Daunoxome®, Ambisome®, and HeparinPur® Liposomal formulations are thought to be especially suitable for application in the lung, as they can be prepared partially or wholly from natural substances endogenous to the lung.

The pharmaceutical term "liposomes" describes a drug delivery vehicle comprised of lipid vesicles, which exhibit a strong structural resemblance to cellular membranes. In the same manner as a cellular membrane, the liposomal vesicles walls (composed often of a phospholipid bilayer) are able to divide an internal aqueous compartment from the external aqueous medium. Liposomes can form spontaneously according to the laws of thermodynamics when, for example, a small amount of phospholipids is dispersed in a larger volume of an aqueous medium. Liposomes are generally prepared from natural, partially synthetic, and synthetic phospholipids. Although other lipids exhibit a cone-shaped molecular structure, which favors micelle formation, phospholipids favor the formation of lamellar structures, due to their cylindrical geometry resulting from the two fatty acid chains of the phopholipid molecule.

The structure of individual liposomal lamellae is similar to that of a cellular membrane. The phospholipids form a bilayer, within which the hydrophobic portions of the molecule extend inwards and the hydrophilic groups interact with the external and internal aqueous phase.

According to their structure and size, liposomes can be divided into several groups (Table 1).

TABLE 1

| Classification | Diameter | Structure |
|---|---|---|
| MLV (multilamellar vesicles) | 100-5000 nm | multiple bilayers |
| SUV (small, unilamellar vesicles) | <100 nm (up to 2000 nm) | small, unilamellar vesicles with a hydrophilic internal compartment |
| LUV (large, unilamellar vesicles) | >100 nm | large, unilamellar vesicles with a hydrophilic internal compartment |

Due to the coexistence of both hydrophilic and hydrophobic regions within liposomes, drug compounds can be incorporated in different ways. Lipophilic compounds accumulate primarily within the lipid bilayer, whereas hydrophilic compounds are generally found either in the aqueous layers between the vesicle bilayer walls or in the aqueous internal compartment. Amphiphilic compounds insert themselves between the phospholipids along the phase interface. The properties of the different liposomal classes determine their applicability. For example, the high amount of lipids found in SUVs make them suitable carriers for lipophilic substances, whereas the large volume of the LUV aqueous internal compartment can hold a high amount of hydrophilic compounds. A sustained release of drug compounds from the liposomal structures is achieved most efficiently with a MLV structure, which requires the compound to cross several diffusion barriers (lipid bilayers) before release.

Both the excellent biocompatibility, as well as the possibility of modifying the pharmacokinetic profile (i.e. through sustained-release formulations) make liposomes a promising vehicle for the controlled and sustained release of drug compounds in the lung.

The development of a formulation based on liposomes for the controlled and sustained release of drug compounds in the lung could be highly relevant for the successful therapy of many diseases. The treatment of lung diseases may especially benefit from the possibility of delivering therapeutic drugs directly to the target organ and, once there, the establishment of a high local drug concentration with a prolonged drug activity at the the site of action. Further, a sustained drug release can lead to a decrease in the number and intensity of side effects by avoiding fluctuations in the drug concentration, as well as concentration peaks immediately after application. Drug encapsulation within liposomes can also protect compounds with a short biological half-life from inactivation before release. In contrast, the encapsulation of compounds with a long biological half-life, such as those used for the treatment of asthma or chronic obstructive pulmonary disease (COPD), may prevent the compound from crossing the air-blood barrier into the systemic circulation and causing systemic side effects. In addition to the previously mentioned lung disorders, asthma and COPD, such lung diseases as pneumonia and pulmonary hypertension are representative of conditions that could be better treated with liposomal drug formulations. For example, the current form of therapy for pulmonary hypertension is based upon the inhalation of vasodilators (i.e. prostacyclin and derivatives thereof). The short biological half-life of these compounds results in the need for frequent sometimes even hourly inhalations, each with a duration of approximately 15 minutes, to achieve a continual, effective pressure reduction in the pulmonary circulation. A sustained-release liposomal formulation for these substances could drastically reduce the frequency of inhalation and guarantee a constant therapeutic reduction in the pulmonary pressure. Both factors would greatly improve patient quality of life.

In addition to the local application of liposomes to treat lung diseases, a controlled and sustained release of drug compounds in the lung may also be of interest for systemic disorders, such as diabetes mellitus. The lung is an organ, which due to its extremely thin air-blood barrier, as well as its large alveolar surface area, has a high capability to absorb drug compounds and allow them to pass into the systemic circulation. For this reason, drug compounds may be applied to the lung for transpulmonary delivery to treat systemic disorders. For example, an aerosolized form of insulin for pulmonary application is currently being developed as an alternative to the subcutaneous insulin injection. However, none of the formulations to date are able to achieve a continual basal insulin release into the circulation.

As of yet, no depot formulation for the pulmonary application of drug compounds has been successfully developed. Currently, the only possibility to achieve a long drug activity in the lung is to apply compounds with adequently long halflives.

The standard method of applying drug compounds to the lung is the inhalation of aerosols. Aerosols containing drug substances can be generated by various methods. The most common devices include air-jet and ultrasonic nebulizers, although metered-dose inhalers and dry powder inhalers are also used. The deposition of the aerosol in the respiratory tract is highly dependent upon particle size distribution of the aerosol droplets. A high percent of particles with an aerodynamic diameter smaller than 6 μm usually reach the trachea, bronchial region, and alveolar space. As a result, only aerosols with aerodynamic diameters smaller than 6 μm should be used for therapeutic purposes.

Drug formulations in aqueous solutions can be aerosolized with air-jet and ultrasonic nebulizers. Metered-dose inhalers and dry powder inhalers require additional formulation modifications (i.e. the solubilization or suspension of the drug in a propellant, micronization of the drug). The aerosolization of aqueous liposomal dispersions can be achieved by air-jet or ultrasonic nebulization. Common to both methods of nebulization is the principle that small aerosol droplets are generated from a liquid reservoir by the application of mechanical energy to the system. The generated aerosol droplets and the liposomal vesicles within them are subjected to aggressive forces which may compromise liposome integrity leading to a premature release of the vesicle contents. Therefore, a sufficient stability of the aerosolized liposome depot formulation is a primary requirement for pulmonary application. The stability of liposomes during nebulization is dependent upon several factors, including technical parameters of the nebulization process (i.e. pressure, ultrasonic frequency) and especially liposome characteristics, such as size, type, and the chemical structure of the lipid components. Another method to administer drug compounds to the lung is an intratracheal instillation. This process involves the insertion of a tube into the trachea or the bronchial region and allowing the drug solution to flow via the tube into the lung. Although this method of application does not require the high stability standards for liposomal formulations as compared to aerosolization, the instillation of a fluid leads to an inhomogeous distribution of the drug solution within the lung. Further, the invasive nature of this application method severely limits its practical use and it cannot be considered suitable for outpatient or long-term treatment. To be considered suitable as a depot formulation for the respiratory tract, a liposomal formulation must possess a sufficient stability during the nebulization process, be able to be incorporated within aerosol droplets smaller than 6 μm, and guarantee a controlled, sustained release of the drug substance at the targeted site of action. The release of the drug substance should ideally begin immediately after deposition of the liposomes in the lung and continue over a period of several hours.

DETAILED DESCRIPTION OF THE INVENTION

In accordance with the present invention, there is provided a specific, non-toxic formulation for pulmonary application, which can be nebulized into aerosol droplets that are able to deposit within the desired regions of the lung. This formulation exhibits a sustained release of encapsulated drug substances and/or dyes after lung deposition. In another aspect of this invention there is provided a method, with which the release of encapsulated drug substance/dye from the said liposomes can be measured.

This objective of this invention is achieved by the disclosure of liposomal formulation parameters containing information about the use of specific liposome-forming lipids endogenous to to the lung combined with synthetic detergents, such as polyethylene glycol and its derivatives. In addition, with the description provided in claim 10, a suitable method for the measurement of encapsulated drug released from the said liposomal formulations is proposed.

The said liposomal formulations are prepared using the so-called "film method" (a detailed description can be found in *Liposomes: A practical approach*, R.R.C. New ed., Oxford University Press, Reprint 1994). In a further step, the liposomes are extruded through a filter membrane and the free, non-encapsulated drug substance is separated from the drug-loaded liposomes via centrifugation, dialysis or chromatographical methods.

To evaluate the encapsulation efficiency, the liposomes can be destroyed by incubation with methanol and the concentration of the released drug substance can be determined with an appropriate method. The evaluation of the stability of liposomes during nebulization is performed by nebulization of a liposomal dispersion with a common nebulizer, collection of the nebulized aerosol, and subsequent quantitative measurement of both the free and encapsulated drug fractions.

Surprisingly, both the common air-jet and ultrasonic nebulizers can generate a high-quality aerosol from the said liposomal formulations. Nebulization of the liposomal dispersions results in an aerosol particle size distribution comparable to that of an isotonic sodium chloride solution. This verifies that the nebulization of liposomal formulations with common commercially available nebulizers can generate aerosol particles, which are able to deposit within the desired regions of the lung. (Examples of commercially available nebulizers include: Air-jet nebulizers, such as the Bennett-Raindrop®, Pari LC®, Pari LL®, and Ventstream®, or ultrasonic nebulizers, such as the Multisonic Pro®, Pulmosonic®, and Systam LS®).

EXAMPLES

Table 2 provides the molar ratios of the components of the said liposomal formulations*. Dipalmitoylphosphatidylcholine (DPPC), cholesterol (Chol), dimyristoylphosphatidylcholine (DMPC), and sphingomyelin (SM) are naturally occurring lipids found within the lung surfactant, whereas polyethylene glycol (PEG) is a synthetic molecule.

TABLE 2

| | Liposomal Formulation | | | | |
|---|---|---|---|---|---|
| | (DPPC) | (Chol) | (PEG) | (DMPC) | (SM) |
| Example 1 | 7 | 3 | 0.15 | — | — |
| | 7 | 3 | 0.3 | — | — |
| | 7 | 3 | 0.6 | — | — |
| Example 2 | 7 | 4 | — | 1 | — |
| | 7 | 4 | — | 2 | — |
| | 7 | 4 | — | 3 | — |
| | 7 | 4 | — | 4 | — |
| Example 3 | 7 | 3 | — | — | 2% |
| | 7 | 3 | — | — | 4% |
| | 7 | 3 | — | — | 6% |
| | 7 | 3 | — | — | 8% |

* The molar ratios of each individual liposome component (DPPC, Chol, DMPC, and PEG) are provided with the exception of SM. In this case, the percent of mass value is listed.

Preperation of Liposomes

Hydrophilic, lipophilic and/or amphiphilic drug compounds/dyes can be encapsulated in the said liposomal formulations and are as such stabilized against aggresive forces during the nebulization process.

In the provided examples, carboxyfluorescein (CF) is used a model drug substance. CF can be detected and quantified via fluorescence spectrometry. The standard CF solution used in the examples is prepared by dissolving 100 mg 5-(6)-carboxyfluorescein in 10 ml phosphate-buffered-saline (PBS) solution and adjusting the pH value to 7.4. Preparation of the the liposomal formulations according to the film method requires 150 mg total lipids (for molar ratios of the lipid components refer to Table 2) to be dissolved in 40 ml cholorform: methanol (70:30) in a round-bottom beaker. The solvent is removed by heating the lipid solution to 60° C. while under rotation and applying a vaccuum. During solvent removal, a thin lipid film is deposited onto the inner beaker wall. The film is allowed to dry under vaccuum for a further two hours, after which 10 ml of the standard CF solution (heated to 60° C.) is added to the beaker to hydrate to film. The resulting dispersion is stirred for two hours at 60° C. and then subjected to a freeze-thaw cycle before extrusion. The freeze-thaw cycle is performed by dipping the beaker into liquid nitrogen until the contents are completely frozen. During the thaw period at room temperature, the lipid membranes tear and fuse together again, encapsulating further CF in the process and, thus, increasing the encapsulation efficiency. This cycle is repeated five times, after which the dispersion is heated to 60° C. in a water bath. Aliquots of 0.5 ml are extruded 21 times through a polycarbonate filter membrane with a pore diameter of 1.0 μm or 0.4 μcm, respectively. The extruded dispersion is subsequently centrifuged four times at 4° C. (4×45 min/4500 rpm or 4×60 min/15,000 rpm, respectively). The free CF in the supernatant is removed after each centrifugation step and replaced with an equal volume of PBS.

Example 1

The liposomal formulations contain a molar ratio of dipalmitoylphosphatidylcholine (DPPC), cholesterol (Chol), and polyethylene glycol (PEG) ranging from 7:3:0.15 to 7:3:0.6.

Example 2

The liposomal formulations contain a molar ratio of dipalmitoylphosphatidylcholine (DPPC), cholesterol (Chol), and dimyristoylphosphatidylcholine (DMPC) ranging from 7:4:1 to 7:4:4.

Example 3

The liposomal formulations contain a molar ratio of dipalmitoylphosphatidylcholine (DPPC) and cholesterol (Chol) of 7:3, corresponding to a percent of mass value equal to 100%. Varying amounts of sphingomyelin (SM) ranging from 2-8% of the total mass were added.

Other liposomal formulations with advantageous properties include liposomes containing dipalmitoylphosphatidylcholine (DPPC) and cholesterol (Chol) with varying amounts of combinations of DMPC, SM, and/or PEG.

The said liposomal formulations exhibit sizes ranging from 0.2-1.5 μm in diameter.

Table 3 shows examples of liposome sizes after preparation, extrusion using a polycarbonate membrane with a pore size of 0.4 um, centrifugation, and nebulization with an air-jet nebulizer (values are provided as the mean±SEM, n=3).

TABLE 3

| Liposomal Formulation | Liposome Diameter After Extrusion (μm) | Liposome Diameter After Centrifugation (μm) | Liposome Diameter After Air-Jet Nebulization (μm) |
|---|---|---|---|
| DPPC:Chol:DMPC 7:4:1 7:4:2 7:4:3 7:4:4 | 0.57 ± 0.01 | 0.58 ± 0.01 | 0.51 ± 0.01 |
| DPPC:Chol:PEG 7:3:0.15 7:3:0.3 7:3:0.6 | 0.60 ± 0.02 | 0.57 ± 0.01 | 0.64 ± 0.01 |
| DPPC:Chol:SM 7:3 with 2% SM 7:3 with 4% SM 7:3 with 6% SM 7:3 with 8% SM | 0.65 ± 0.01 | 0.68 ± 0.02 | 0.70 ± 0.01 |

Stability of the Liposomal Formulations During Nebulization

To determine whether liposomes are stable during nebulization, a liposomal formulation (extruded using a polycarbonate filter membrane with a pore size of 0.4 μm) is diluted with PBS at a ratio of 1:10 and aliquots of 2.5 ml of the diluted dispersion are nebulized for three minutes at room temperature using an air-jet nebulizer (driven with 1 bar compressed air) and an ultrasonic nebulizer (driven with an air-flow of 10 l/min). The generated aerosol is diverted through a silicone tube (15 cm long, 3 cm inner diameter) onto which end a glass plate is attached. The aerosol condenses on the glass plate and the condensate is collected in a 40 ml beaker. The fractions of free and encapsulated CF in the collected dispersions is determined via fluorescence spectrometry.

The determination of the amount of free CF ($CF_{free}$) is performed as follows: 100 μl of the said liposomal dispersion is centrifuged in an Eppendorf tube. 50 μl of the supernatant is subsequently diluted 1:100 with PBS and the CF concentration is determined via fluorescence spectrometry. Determination of the total amount of CF ($CF_{total}$) in the said liposomal formulation is performed as follows: 450 μl methanol is added to 50 μl liposome dispersion, the mixture is incubated for 10 min., and centrifuged. The addition of methanol destroys the liposome structure and achieves a complete release of all encapsulated substances. Following centrifugation, 50 μl of the supernatant is diluted 1:1000 with PBS and the concentration of CF is determined via fluorescence spectrometry. The amount of encapsulated CF can be calculated using the following equation:

$$c_{encapsulated}=(c_{total}-c_{free})*100/c_{total}[\%]$$

Studies evaluating the stability of liposomes during nebulization show that 50%-80% of the liposomal population remain intact during nebulization with air-jet and ultrasonic nebulizers.

Table 4 shows examples of the stability of liposomes during air-jet nebulization (values are provided as the mean±SEM, n=4).

TABLE 4

| Liposomal Formulation | Amount of Encapsulated Drug Substance After Nebulization (%) |
|---|---|
| DPPC:Chol:DMPC<br>7:4:1<br>7:4:2<br>7:4:3<br>7:4:4 | 69.3 ± 1.3 |
| DPPC:Chol:PEG<br>7:3:0.15<br>7:3:0.3<br>7:3:0.6 | 55.7 ± 1.8 |
| DPPC:Chol:SM<br>7:3 with 2% SM<br>7:3 with 4% SM<br>7:3 with 6% SM<br>7:3 with 8% SM | 76.9 ± 0.7 |

Release Kinetics of Encapsulated Drug Substances from Liposomal Formulations in a Lung Model The said liposomal dispersions can be tested in an isolated, perfused rabbit lung model (Seeger et al., J Appl Physiology 1986, 61:1781-1789; Seeger et al., In: *Oxygen Radicals in Biological Systems*, L. Packer Ed. New York: Academic Press, 1994, vol. 233:549-584). Rabbits weighing 2.5-3 kg are administered the anticoagulant, heparin, and anaesthized with a mixture of xylocaine, ketamine, and xylazine. A tracheostomy is performed under controlled ventilation with air. Following a central, sternal thoracotomy, the pulmonary artery is catheterized, the aorta ligated, and both ventricles opened at the bottom tip.

The lung is perfused using a cylindrical pump. The perfusate is composed of a Krebs-Henseleit electrolyte solution containing hydroxyethylated starch and sodium bicarbonate. Parallel to the artificial perfusion, the lung is ventilated with a mixture of 21% oxygen, 5.3% carbon dioxide, and 73.7% nitrogen. The heart and lungs are carefully removed from the chest cavity and a second catheter is immobilized in the left ventricle via a circular stitch. After the lung is hung in a chamber on a scale, the venous section of the perfusion system is connected to the catheter in the heart creating a closed, recirculating perfusion system. The perfusate is kept at a constant physiological temperature by heating the fluid to 38° C. The isolated lung is also kept at a physiological temperature by heating the air of the chamber to 38° C., as well.

The standard parameters of the lung ventilation and perfusion are as follows:

The rate of perfusion controlled by the speed of the cylindrical pumps is 100 ml/min.

Lung ventilation is performed using an inspiratory volume of 30 ml and an inspiratory frequency of 30 $min^{-1}$.

The positive end expiratory pressure (PEEP) is 1 mmHg.

The left ventricular pressure is held constant at 2 mmHg.

The perfusate volume is 150 ml.

The inhalative application of aerosols is performed using the so-called "bag-in-box" system (FIG. 1). This system is comprised of an air-jet nebulizer (1), reservoir bag (2), valve (3), and a flexible balloon (4, bag) contained within an air-tight glass case (5, box). The ventilation pump is attached to the glass case (5) and creates an environment of either high or low pressure within the balloon (4) according to the direction of the gas flow. The aerosol generated by the air-jet nebulizer (1) is initially directed into the reservoir bag. During the expiratory phase of the pump (6), the flexible balloon (4) expands as a result of the lowered pressure in the glass case (5). A valve system (3) connecting the flexible balloon (4) to the reservoir bag (2) allows the aerosol to pass from the reservoir to the balloon upon expansion. During the subsequent inspiratory phase of the pump (6), the valve (3) closes and the aerosol is pressed from the collapsing bag (4) into the lung (7).

Nebulization is carried out by an air-jet nebulizer (Bennett-Raindrop®) operated at, a pressure of 1 bar with an air mixture of 5.3% $CO_2$, 21% $O_2$, and 73.7% $N_2$.

An initial series of measurements to determine the release kinetics of encapsulated drug substances or dyes from liposomes involves two sequential interventions in the lung. First, a defined amount of aerosolized CF solution is applied to the lung within a time period of 30 minutes, followed by a period of observation of 90 minutes. The perfusate is then exchanged with one liter fresh electrolyte solution and the aerosolized liposomal formulation is applied to the lung over a time period of 30 minutes. This is following by a period of observation of up to 270 minutes. An equal amount of CF is deposited in the lung during both inhalative aerosol applications. Free CF is known to cross the alveolar barrier into the the lung circulation rapidly and completely. By removing 0.5 ml samples from the perfusate, beginning at a time point just before aerosol application and repeating this step every ten minutes thereafter, the amount of dye crossing the alveolar barrier may be quantified. A comparison with the free CF profile permits an evaluation of the release kinetics of the encapsulated dye from the liposomal formulation.

The release kinetics of the model drug, CF, from the said liposomal formulations are depicted in FIGS. 2-4 (FIG. 2 Release kinetics from DPPC/Chol/DMPC liposomes, FIG. 3 Release kinetics from DPPC/Chol/PEG liposomes, FIG. 4 Release kinetics from DPPC/Chol/SM liposomes).

Figure 1:
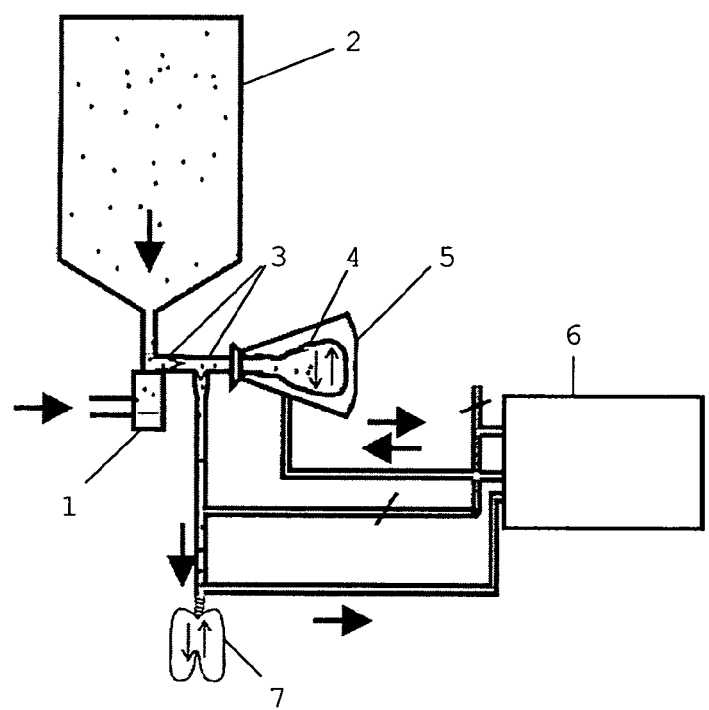
FIG. 1. Depiction of the "Bag-in-Box" system used to ventilate the isolated lung.

The ventilation pump (6) controls the movement of a flexible balloon (4), which provides the lung (7) with the aerosol/gas mixture from a reservoir bag (2). The reservoir bag is filled with the aerosol generated by an air-jet nebulizer (1) operated with compressed air at a pressure of 1.0 bar.

Figure 2:
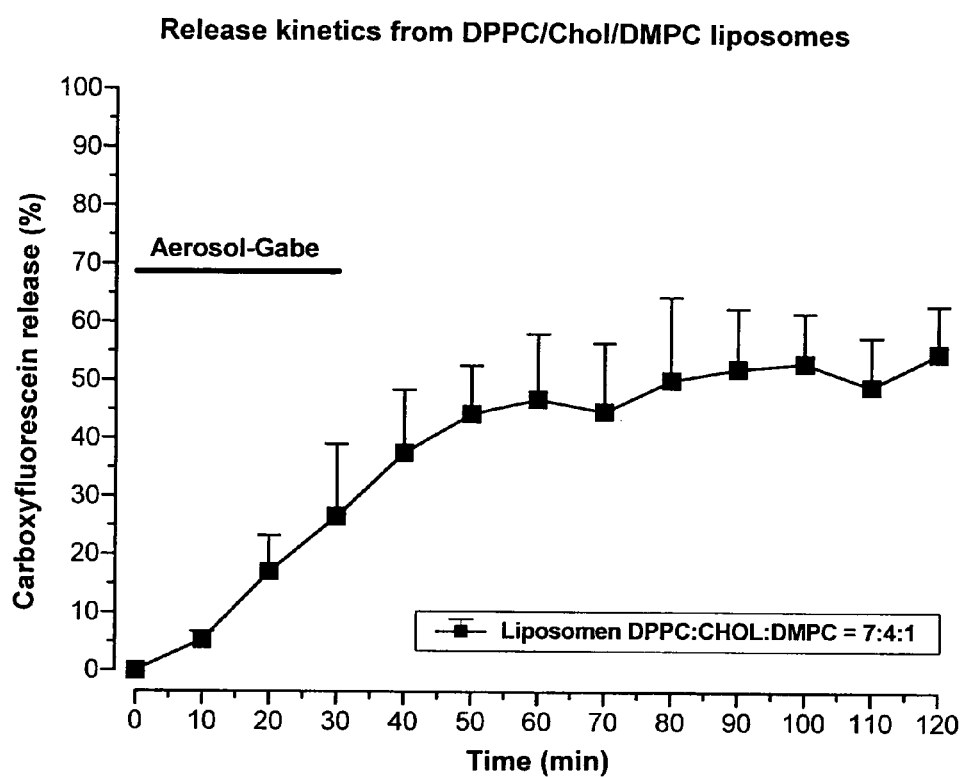

FIG. 2. Release kinetics from DPPC/Chol/DMPC liposomes.

Figure 3:
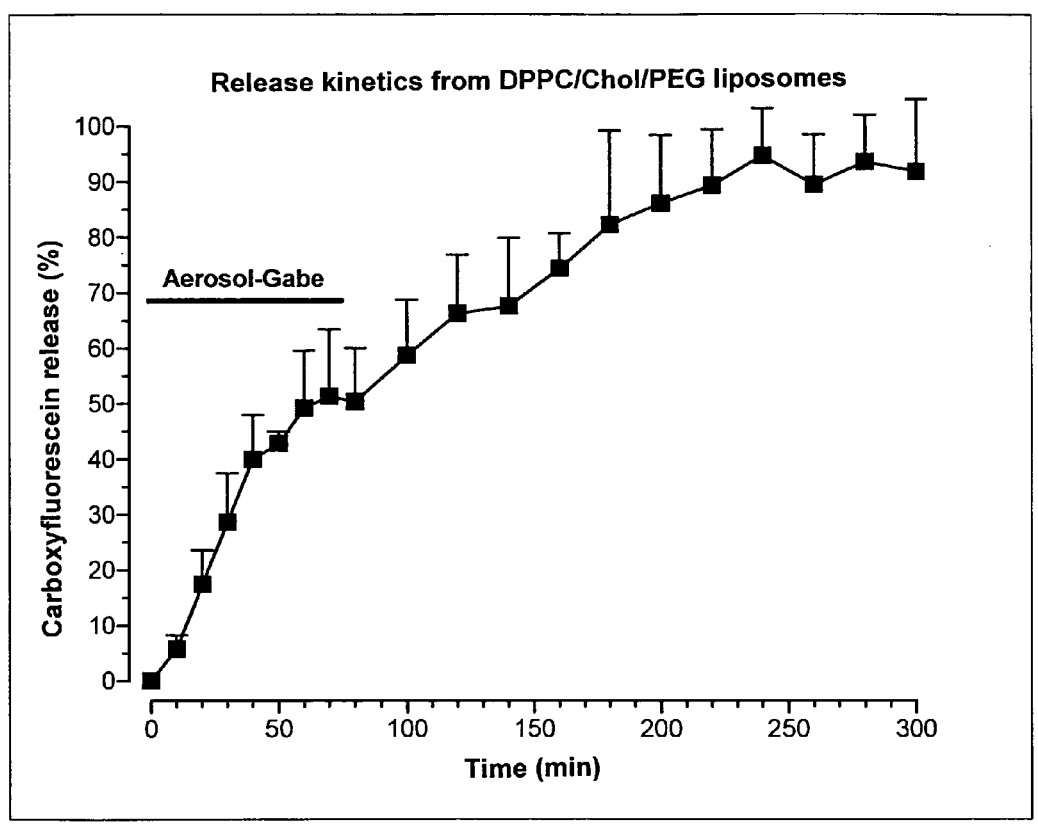

Liposomes composed of DPPC:Chol:DMPC=7:4:1 and containing carboxyfluorescein as a model drug are applied to a ventilated, isolated, perfused rabbit lung over a period of 30 min in an aerosolized form. The amount of carboxyfluorescein released from the liposomes and determined in the perfusate is given as the percent of total amount of carboxyfluorescein initially present within the liposomal formulation. Values provided are the mean±SEM from n=3 experiments. DPPC=Dipalmitoylphosphatidylcholine, Chol=Cholesterol, DMPC=Dimyristoylphosphatidylcholine FIG. 3. Release kinetics from DPPC/Chol/PEG liposomes.

Liposomes composed of DPPC:Chol:PEG=7:4:0.3 and containing carboxyfluorescein as a model drug are applied to a ventilated, isolated, perfused rabbit lung over a period of 30 min in an aerosolized form. The amount of carboxyfluorescein released from the liposomes and determined in the perfusate is given as the percent of total amount of carboxyfluorescein initially present within the liposomal formulation. Values provided are the mean±SEM from n=3 experiments.

DPPC=Dipalmitoylphosphatidylcholine, Chol=Cholesterol, PEG=Polyethylene glycol

Figure 4:
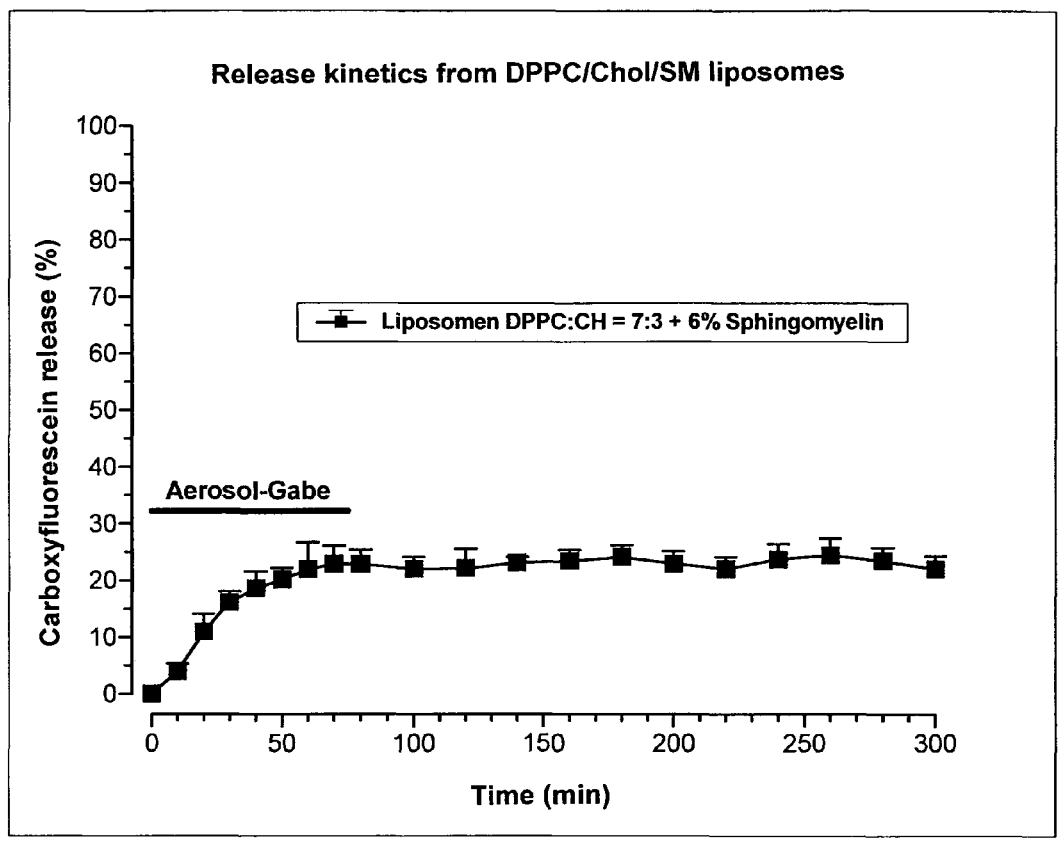

FIG. 4. Release kinetics from DPPC/Chol/SM liposomes.

Liposomes composed of DPPC:Chol:SM=7:3 plus 6% sphingomyelin and containing carboxyfluorescein as a model drug are applied to a ventilated, isolated, perfused rabbit lung over a period of 30 min in an aerosolized form. The amount of carboxyfluorescein released from the liposomes and determined in the perfusate is given as the percent of total amount of carboxyfluorescein initially present within the liposomal formulation. Values provided are the mean±SEM from n=3 experiments.

DPPC=Dipalmitoylphosphatidylcholine, Chol=Cholesterol, SM=Sphingomyelin

LEGEND (1): Air-jet nebulizer
(2): Reservoir bag
(3): Valve
(4): Flexible balloon
(5): Glass case
(6): Ventilation pump
(7): Lung

The invention claimed is:

1. A method of pulmonary administration comprising administering to a subject in need thereof via inhalation via a nebulizer a liposomal formulation comprising:
    a) liposomes, that comprise as a first component dipalmitoylphosphatdylcholine (DPPC) lipids, as a second component cholesterol (CH) lipids, and a third component selected from the group consisting of dimyristoylphosphatidylcholine (DMPC) lipids, sphingomyelin (SM) lipids and polyethylene glycol (PEG) and PEG derivatives and
    b) an active agent encapsulated inside the liposomes,
    wherein a molar ratio between the DPPC lipids and the CH lipids ranges from 7:3 to 7:4 and wherein upon said administering 50-80% of the liposomes remain intact.

2. The method of claim 1, wherein said liposomes consist of the first component, the second component and the third component.

3. The method of claim 1, wherein the third component is selected from the group consisting of DMPC lipids and the SM lipids.

4. The method of claim 3, wherein the third component is the DMPC lipids.

5. The method of claim 4, wherein a molar between the DPPC lipids and the DMPC lipids in the liposomes ranges from 7:1 to 7:4.

6. The method of claim 3, wherein the third component is the SM lipids.

7. The method of claim 6, wherein the liposomes contain from 2% to 8% of the SM lipids by mass.

8. The method of claim 1, wherein the third component is the PEG.

9. The method of claim 1, wherein a molar ratio between the DPPC lipids and the PEG ranges from 7:0.15 to 7:0.6.

10. The method of claim 1, wherein the nebulizer is an ultrasonic nebulizer.

11. The method of claim 1, wherein the nebulizer is an air-jet nebulizer.

12. The method of claim 1, wherein the active agent is a drug compound.

13. The method of claim 12, wherein the active agent is an inhalable vasodilator, which is prostacyclin or a derivative thereof.

14. The method of claim 12, wherein the active agent is a prostacyclin.

15. The method of claim 1, wherein the active agent is a dye.

16. The method of claim 1, wherein said liposomes are multilamellar vesicles.

17. A method of treating a pulmonary or systemic disease comprising administering to a subject in need thereof via inhalation via a nebulizer a liposomal formulation comprising a) liposomes, that comprise a first component, that is dipalmitoylphosphatdylcholine (DPPC) lipids, a second component, that is cholesterol (CH) lipids, and a third component, that is selected from dimyristoylphosphatidylcholine (DMPC) lipids, sphingomyelin (SM) lipids and polyethylene glycol (PEG) and PEG derivatives and b) an active agent encapsulated inside the liposomes wherein a molar ratio between the DPPC lipids and the CH lipids ranges from 7:3 to 7:4 and wherein upon said administering 50-80% of the liposomes remain intact.

18. The method of claim 17, wherein said liposomes consist of the first component, the second component and the third component.

19. The method of claim 17, wherein the third component is selected from the DMPC lipids and the SM lipids.

20. The method of claim 19, wherein the third component is the DMPC lipids.

21. The method of claim 20, wherein a molar between the DPPC lipids and the DMPC lipids in the liposomes ranges from 7:1 to 7:4.

22. The method of claim 19, wherein the third component is the SM lipids.

23. The method of claim 22, wherein the liposomes contain from 2% to 8% of the SM lipids by mass.

24. The method of claim 17, wherein the third component is the PEG.

25. The method of claim 24, wherein a molar ratio between the DPPC lipids and the PEG ranges from 7:0.15 to 7:0.6.

26. The method of claim 17, wherein the nebulizer is an ultrasonic nebulizer.

27. The method of claim 17, wherein the nebulizer is an air jet nebulizer.

28. The method of claim 17, wherein the active agent is a drug compound.

29. The method of claim 28, wherein the active agent is prostacyclin or a derivative thereof.

30. The method of claim 17, wherein the active agent is a dye.

31. The method of claim 17, wherein the disease is pulmonary hypertension.

* * * * *